(12) United States Patent (10) Patent No.: US 12,661,314 B2
Schmitz et al. (45) Date of Patent: Jun. 23, 2026

(54) MULTI-LAYER ORAL THIN FILM

(71) Applicant: LTS LOHMANN THERAPIE-SYSTEME AG, Andernach (DE)

(72) Inventors: Christoph Schmitz, Rheinbrohl (DE); Michael Linn, Waldbockelheim (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 9 days.

(21) Appl. No.: 16/964,351

(22) PCT Filed: Jan. 28, 2019

(86) PCT No.: PCT/EP2019/051960
§ 371 (c)(1),
(2) Date: Jul. 23, 2020

(87) PCT Pub. No.: WO2019/145524
PCT Pub. Date: Aug. 1, 2019

(65) Prior Publication Data
US 2021/0030668 A1 Feb. 4, 2021

(30) Foreign Application Priority Data
Jan. 26, 2018 (DE) ..................... 10 2018 101 778.2

(51) Int. Cl.
*A61K 9/00* (2006.01)

(52) U.S. Cl.
CPC ................................. *A61K 9/0056* (2013.01)

(58) Field of Classification Search
CPC .... A61K 9/0056; A61K 9/7007; A61K 9/006; A61K 47/10; A61K 47/32; A61K 47/36; A61K 47/34; A61K 9/70; A61K 47/30
See application file for complete search history.

(56) References Cited

U.S. PATENT DOCUMENTS

| | | | |
|---|---|---|---|
| 5,914,118 A | 6/1999 | Yamamura et al. | |
| 7,276,246 B2 * | 10/2007 | Zhang | A61K 9/006 |
| | | | 424/434 |
| 2005/0048102 A1 * | 3/2005 | Tapolsky | A61K 9/006 |
| | | | 424/448 |
| 2008/0026040 A1 * | 1/2008 | Farr | A61K 31/18 |
| | | | 424/443 |
| 2010/0112015 A1 | 5/2010 | Nogami | |
| 2011/0200715 A1 | 8/2011 | Fuisz et al. | |
| 2011/0290694 A1 | 12/2011 | Fuisz et al. | |
| 2013/0017235 A1 | 1/2013 | Nogami | |
| 2013/0039967 A1 | 2/2013 | Meyer et al. | |
| 2014/0261990 A1 * | 9/2014 | Dadey | B32B 7/06 |
| | | | 156/227 |
| 2018/0036251 A1 | 2/2018 | Bogdahn et al. | |

FOREIGN PATENT DOCUMENTS

| | | | | |
|---|---|---|---|---|
| CN | 1407886 A | 4/2003 | | |
| CN | 101370477 A | 2/2009 | | |
| CN | 101534803 A | 9/2009 | | |
| CN | 103153613 A | 6/2013 | | |
| DE | 102014119576 A1 | 6/2016 | | |
| JP | H11500725 A | 1/1999 | | |
| JP | 2004248665 A | * | 9/2004 | |
| JP | 2009120497 A | 6/2009 | | |
| JP | 2011050394 A | 3/2011 | | |
| JP | 2016505579 A | 2/2016 | | |
| WO | 2006039264 A1 | 4/2006 | | |
| WO | WO 2009125465 A | * | 10/2009 | |
| WO | WO-2009125465 A1 | * | 10/2009 | A61J 3/078 |
| WO | 2011134846 A1 | 11/2011 | | |
| WO | 2013100564 A1 | 4/2013 | | |

OTHER PUBLICATIONS

Office Action for German Application No. 10 2018 101 778.2, dated Nov. 16, 2021, 8 pages.
Office Action for Japanese Application No. 2020-560599, mailed Dec. 7, 2021, 4 pages.
Office Action for Chinese Patent Application 201980009860.2 mailed on Jan. 28, 2023.
Notice of Allowance for South Korean Patent Application No. 1020207023825, dated Apr. 30, 2024, 3 pages.

* cited by examiner

*Primary Examiner* — Walter E Webb
*Assistant Examiner* — Colman Thomas Welles
(74) *Attorney, Agent, or Firm* — Lippes Mathias LLP

(57) ABSTRACT

Described are: a multi-layer oral thin film, comprising at least two layers arranged one on top of the other, which each comprise at least one water-soluble polymer, these at least two layers being connected to one another by at least one sealing, characterised in that the at least one sealing is not provided over the entire surface; a method for producing same; and use thereof as a medicament.

14 Claims, 1 Drawing Sheet

1a  1b  1c  1d  1e
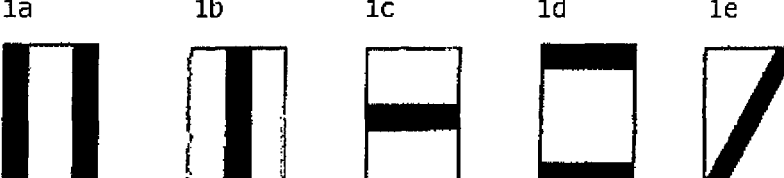

MULTI-LAYER ORAL THIN FILM

The present invention relates to a multi-layer oral thin film, to a method for producing same, and to the use thereof as a medicament.

Oral thin films are thin films containing a pharmaceutically active ingredient which are placed directly in the oral cavity or are placed against the oral mucosa and dissolve there. In particular, they are thin active-ingredient-containing, polymer-based films, which, when applied to a mucosa, in particular the oral mucosa, deliver the active ingredient directly into the mucosa. These oral thin films are generally not sticky on the outside. The very good blood supply to the oral mucosa ensures a quick transfer of the active ingredient into the bloodstream. This delivery system has the advantage that the active ingredient is absorbed for the most part by the mucosa, and therefore the first-pass metabolism, which occurs with the conventional tablet dosage form of an active ingredient, these generally being administered together with liquid, which may be disadvantageous, is avoided. The active ingredient may be dissolved, emulsified or dispersed in the film. Suitable active ingredients may also be swallowed once the oral thin film has dissolved in the mouth, and thus may be absorbed via the gastrointestinal tract.

The oral thin films known from the prior art have the disadvantage that the maximum weight per area unit and therefore the amount of contained pharmaceutically active ingredient is determined by the drying of the oral thin film during its production. The greater the weight per unit area of the oral thin film, the more pharmaceutically active ingredient may be contained therein, however the drying time of the oral thin film is then extended as a result to a time that is no longer economical. This disadvantage may, indeed, be counteracted by an increased drying temperature, however the pharmaceutically active ingredient will thus be exposed to an undesirable thermal loading. In addition, oral thin films with a high weight per unit area have a relatively long disintegration time, which may be undesirable depending on the application.

The above-mentioned problems may be overcome in principle by multi-layer oral thin films.

Multi-layer oral thin films are known from the prior art.

Document WO 2011/134846 A1 discloses multi-layer oral thin films comprising an active-ingredient-containing layer and a layer containing a substance that is incompatible with the active ingredient in the active-ingredient-containing layer, these two layers being separated by a further protective layer situated between these two layers.

US 2013/0017235 A1 discloses multi-layer oral thin films in which an active-ingredient-containing layer is enclosed by two water-swellable polymer layers.

The known multi-layer oral thin films, however, in which a plurality of individual layers with a relatively lower weight per unit area are adhesively bonded or laminated to form a composite structure, have a number of disadvantages. On the one hand, greater amounts of suitable adhesives sometimes have to be used between the layers. On the other hand, such multi-layer systems may be produced by firstly producing a first layer and, once this has dried, laminating a second layer onto the first layer. Once the second layer has dried on the first layer, a third layer may then be laminated on if necessary. Multi-layer thin films may indeed be provided by such a method, but only by the lamination of further layers onto an existing layer. This in turn has the disadvantage that the pharmaceutically active ingredient is subjected to a stronger thermal loading on account of the multiple coating processes. In addition, a composite structure created by lamination, in particular if the individual layers of the oral thin film are not sticky, is often unstable and may easily disaggregate.

The aim of the present invention lies in overcoming the above-mentioned disadvantages of the prior art. Especially, the aim of the present invention lies in providing a multi-layer oral thin film which is constructed from a plurality of individual layers having a relatively low weight per unit area which are fixedly connected to one another so that the individual layers may be dried in an economically acceptable time and the pharmaceutically active ingredient is subjected to a lower thermal loading. in addition, the multi-layer oral thin film will dissolve relatively quickly in the case of application in the oral cavity.

The above aim is addressed by a multi-layer oral thin film according to claim 1, wherein the multi-layer oral thin film comprises at least two layers arranged one on top of the other, each comprising at least one water-soluble polymer, said at least two layers being connected to one another by at least one sealing, said at least one sealing not being provided over the entire surface.

A multi-layer oral thin film of this construction is characterised in that, due to the use of a number of layers, the amount of pharmaceutically active ingredient, in relation to the total oral thin film, may be increased without the need for long drying times or without having to accept a thermal loading of the pharmaceutically active ingredient. Especially, it is thus possible, to the greatest possible extent, to prevent the oral thin film, for drying, from being exposed over a relatively long time, especially longer than approximately 20 minutes, to temperatures as are usually used for the drying of oral thin films, especially temperatures greater than approximately 70° C.

Especially, the multi-layer oral thin film according to the invention, due to the sealing not provided over the entire surface, has a much larger surface as compared to conventional oral thin films. Due to the larger surface, the multi-layer oral thin film according to the invention dissolves much more quickly in the case of application in the oral cavity. Especially due to the sealing not provided over the entire surface, saliva may infiltrate between the individual layers, thus causing the oral thin film to dissolve more quickly.

BRIEF DESCRIPTION OF THE DRAWINGS

FIGS. 1*a*-1*e* are schematic depictions of multi-layer oral thin films according to the invention, wherein the individual layers are connected to one another by one or two sealings not provided over the entire surface.

Water-soluble polymers comprise chemically very different natural or synthetic polymers, the common feature of which is their solubility in water or aqueous media. A precondition for this is that these polymers have a number of hydrophilic groups sufficient for the water-solubility and are not cross-linked. The hydrophilic groups may be non-ionic, anionic, cationic and/or zwitterionic.

A sealing is understood to mean any possible method by which at least two layers of the multi-layer oral thin film may be connected to one another, with each layer comprising at least one water-soluble polymer. For example, this includes connections by adhesive bonding, embossing, lamination and/or heat sealing, although these examples are not exhaustive.

A sealing not provided over the entire surface is understood to mean that the area by which the at least two layers of the multi-layer oral thin film are connected to one another is smaller than the surface of one side of a layer of the multi-layer oral thin film. This sealing not provided over the entire surface may be provided in the form of one or more continuous strips over the surface of the multi-layer oral thin film, or by a sealing at one or more separate points.

The at least two layers, which may each comprise at least one water-soluble polymer, may have the same or a different composition. The at least two layers, which each comprise at least one water-soluble polymer, may also have the same or a different size or area. In addition, the at least two layers, which comprise at least one water-soluble polymer, may have the same or a different weight per unit area.

It is preferred that at least one of the overlapping edges of the at feast two layers arranged one on top of the other is not closed by a sealing. This has the advantage that saliva may easily infiltrate from outside between the individual layers, which expedites the dissolution of the multi-layer oral thin film according to the invention.

The at least two layers of the oral thin film according to the invention preferably have the same size or area.

If the at least two layers of the oral thin film according to the invention have the same size or area, it is preferred that the at least two layers are arranged congruently one on top of the other so that the edges of the at least two layers overlap and neither of the at least two layers protrudes beyond the other.

However, embodiments of the oral thin film according to the invention in which the at least two layers are misaligned with one another so that they are not arranged congruently one on top of the other are also conceivable.

In addition, embodiments of the oral thin film according to the invention in which the at least two layers have a different size or area are conceivable.

Furthermore, the multi-layer oral thin film according to the invention is characterised in that the at least one sealing not provided over the entire surface comprises a heat-sealing not applied over the entire surface.

The multi-layer oral thin film according to the invention is therefore preferably characterised in that the at least one polymer comprises a heat-sealable polymer.

Heat sealing is understood to mean a connection of the at least two layers arranged one on top of the other of the multi-layer oral thin film by a heating and pressing, at specific points, of the at least two layers arranged one on top of the other. By heating at specific points, the at least one polymer which is provided in each of the individual layers of the multi-layer oral thin film melts, and, once cooled down again, leads to a fixed connection of the at least two layers. The specific points are preferably heated to a temperature that lies above the melting point or glass transition temperature of the polymer in question.

Usual temperatures for heat sealing are approximately 50° C. to 200° C.

During the heat sealing, the oral thin film is preferably heated for approximately 5 seconds, preferably approximately 3 seconds, and especially preferably approximately 2 seconds or less, to a temperature of approximately 50° C. to 200° C.

As a result of these very short times, which are required for the heat sealing, the thermal loading of the at least one pharmaceutically active ingredient is less severe than with longer drying temperatures as described above.

A heat-sealable polymer is therefore understood to be a polymer that may be melted or softened by being heated at specific points, so that a connection may be produced to layers arranged above or below.

The at least one water-soluble polymer preferably comprises polyvinyl alcohol, pullulan, polyethylene oxide and/or polyethylene glycol, and copolymers thereof.

These polymers have the advantage that they are compatible with a large number of pharmaceutically active ingredients and in addition are largely safe for a patient for whose treatment the multi-layer oral thin film according to the invention is used.

In addition, the described polymers are preferred since they are heat-sealable.

The multi-layer oral thin film according to the invention is additionally preferably characterised in that at least one layer of the multi-layer oral thin film comprises at least one pharmaceutical active ingredient.

The pharmaceutically active ingredient may be contained in the multi-layer oral thin film according to the invention in principle in each of the layers of the multi-layer oral thin film according to the invention, with consideration being taken of the compatibility of the active ingredient in question with the material from which a particular layer is formed and, as applicable, also with the material from which the other layers are formed.

The multi-layer oral thin film according to the invention is not limited to the fact that only one pharmaceutically active ingredient is contained. Multi-layer oral thin films in which different pharmaceutically active ingredients are contained in different layers are thus conceivable. An individual layer may also contain more than one pharmaceutically active ingredient.

The present invention is particularly advantageous in respect of a multi-layer oral thin film which contains different active ingredients in different layers. In accordance with the invention, these different layers may all be produced separately and then connected to one another in accordance with a modular principle by a sealing not provided over the entire surface.

Generally, any pharmaceutically active ingredient that is suitable for transmucosal or oral administration may be contained in the multi-layer oral thin film according to the invention.

The at least one pharmaceutically active ingredient is preferably a pharmaceutically active ingredient that is selected from the group consisting of pharmaceutically active ingredients that are suitable for oral applications in the context of the present invention. These are, for example, anti-allergic agents, anti-arrhythmic agents, antibiotics, anti-diabetic agents, anti-epileptic agents, antihistamines, anti-tussives, cardiotonic agents, diuretics, anti-hypertensive agents, anaesthetics, nerve muscle blockers and sex hormones, such as vasopressors. Specific examples are acet-aminophen, adrenalin, alprazolam, amlodipine, anastrozole, apomorphine, aripiprazole, atorvastatin, baclofen, benzo-caine, benzocaine/menthol, benzydamine, buprenorphine, buprenorphine/naloxone, buprenorphine/naloxone/cetiriz-ine, cetirizine, chlorpheniramine, clomipramine, dexam-ethasone, dextromethorphan, dextromethorphan/phenyleph-rine, diclofenac, diphenhydramine, diphenhydramine/phenylephrine, donepezil dronabinol, epinephrine, escitalopram, famotidine, fentanyl, glimepiride, GLP-1 pep-tides, granisetron, insulin, insulin nanoparticles, insulin/GLP-1 nanoparticles, ketoprofen, ketotifen, caffeine, levo-cetirizine, loperamide, loratadine, meclizine, methylphenidate, midazolam, mirodenafil, montelukast, multimeric-001, naloxone, nicotine, nitroglycerine, olanzap-ine, olopatadine, ondansetron, oxybutynin, pectin, pectin/menthol, pectin/ascorbic acid, PediaSUNAT (artesunate and amodiaquine), piroxicam, phenylephrine, prednisolone, pseudoephedrine, risperidone, rivastigmine, rizatriptan, selegiline, senna glycosides, sildenafil citrate, simethicone, sumatriptan, tadalafil, testosterone, triamcinolone acetonide, triptan, tropicamide, voglibose, zolmitriptan, zolpidem, or pharmaceutically acceptable salts of these compounds. As non-pharmaceutical active ingredients, the dosage form according to the invention may contain, for example, active ingredients for oral hygiene, such as menthol. The pharmaceutical active ingredient may also be a mixture of different active ingredients.

The at least one pharmaceutically active ingredient is in principle contained at least in a pharmaceutically effective amount in at least one of the layers of the multi-layer oral thin film according to the invention.

It is preferred if the pharmaceutically active ingredient is present in at least one layer of the multi-layer oral thin film in an amount of from 1 to 60 wt. %.

In principle, the number of individual sealings for connection of the individual layers of the multi-layer oral thin film according to the invention is not limited, provided the sum of the individual areas of the sealings is smaller than the area of a side of the multi-layer oral thin film according to the invention.

If the at least two layers arranged one on top of the other which comprise at least one water-soluble polymer have a different size or area, the area of the sealing must be smaller than the area of the smallest layer.

It is preferred that the at feast two layers are connected to one another by a sealing not provided over the entire surface.

In addition, it is preferred if the oral thin film according to the invention is characterised in that the at least two layers are connected to one another by two sealings not provided over the entire surface.

The multi-layer oral thin film according to the invention is preferably characterised in that the at least one sealing comprises no more than approximately 66% of the total area of a surface of the multi-layer oral thin film.

If the at least two layers which comprise at least one water-soluble polymer have a different size or area, the values in % then relate to the area of the smallest layer.

If the area of the sealing is smaller, this has the disadvantage that the individual layers of the oral thin film are not fixedly connected to one another. If the area is larger, this has the disadvantage that the total surface of the oral thin film decreases.

The form of the at least one sealing not applied over the entire surface is not limited. The sealing is expediently carried out in strip form and/or dot form.

Schematic depictions of multi-layer oral thin films according to the invention, wherein the individual layers are connected to one another by one or two sealings not provided over the entire surface, are shown in FIGS. 1a to 1e.

The multi-layer oral thin film according to the invention is furthermore preferably characterised in that the at least two non-sticky layers each have a weight per unit area of from 20 to 300 g/m².

If the weight per unit area is greater, this has the disadvantage of especially long drying times, which is disadvantageous from an economical viewpoint. In addition, bubbles may form as a result of the forming of a skin. A film having a lower weight per unit area is only able to be processed with difficulty.

In addition, conventional additives such as permeation enhancers, antioxidants, flavourings, taste-masking agents, preservatives, colourings, inert fillers, etc. may be contained in the various layers of the multi-layer oral thin film according to the invention.

The present invention also relates to a method for producing a multi-layer oral thin film as defined above, comprising the steps of a) providing a first layer comprising at least one water-soluble polymer;

b) providing a further layer comprising at least one water-soluble polymer;

c) arranging the first layer on the further layer; and d) performing at least one sealing, which is not provided over the entire surface, in order to connect the first layer and the further layer to one another.

Embodiments are conceivable in which the first and the further layer have the same composition. Embodiments in which the first and the further layer have different compositions are also conceivable.

In the method according to the invention it is additionally preferred that at least one of the layers provided in step a) and/or step b) additionally comprises at least one pharmaceutical active ingredient.

In addition, the method according to the invention is advantageously characterised in that the at least one sealing performed in step d), not provided over the entire surface, is a heat-sealing not provided over the entire surface.

In a possible embodiment the first layer (a) has the same composition as the further layer (b).

In a further possible embodiment, the first layer a) has a different composition as compared to the further layer (b).

In a possible embodiment the first layer a) and/or the further layer b) already comprise more than one layer. Multi-layer oral thin films that comprise at least three layers are thus obtainable.

In principle, multi-layer oral thin films which have at least two layers, but also any number of layers, may thus be provided by the method according to the invention.

The present invention additionally relates to a multi-layer oral thin film obtainable in accordance with the method described above.

The present invention also relates to a multi-layer oral thin film as described above or as obtainable in accordance with the method described hereinafter, for use as a medicament.

The invention will be explained hereinafter with reference to non-limiting examples.

EXAMPLES

Schematic depictions of possible multi-layer oral thin films according to the invention, wherein the particular sealing(s), not provided over the entire surface, which has/have been used to connect the individual layers in the multi-layer oral thin film according to the invention is/are highlighted schematically by the dark shading, are shown in FIGS. 1a to 1e.

The invention claimed is:

1. A multi-layer oral thin film comprising at least two layers having the same size or area arranged one on top of the other, wherein each layer comprises at least one water-soluble polymer, the at least two layers being connected to one another by at least one sealing, wherein the at least one sealing is not provided over an entire surface, and wherein that the at least one sealing is applied in such a way that at least one overlapping edge of the at least two layers arranged one on top of the other is not closed by a sealing as to allow saliva to infiltrate between the individual layers, wherein at least one layer of the multi-layer oral thin film comprises at least one pharmaceutical active ingredient, wherein the at least one sealing comprises no more than approximately 66% of the total area of a surface of the multi-layer oral thin film, wherein at least one pharmaceutically active ingredient is contained within at least one layer of the multi-layer oral thin film.

2. The multi-layer oral thin film according to claim 1, wherein the at least one water-soluble polymer comprises a heat-sealable polymer.

3. The multi-layer oral thin film according to claim 2, wherein the at least one sealing not provided over the entire surface comprises a heat sealing not provided over the entire surface.

4. The multi-layer oral thin film according to claim 1, wherein the at least one water-soluble polymer comprises polyvinyl alcohol, pullulan, polyethylene oxide, polyethylene glycol and/or copolymers thereof.

5. The multi-layer oral thin film according to claim 1, wherein the at least two layers are connected to one another by precisely one sealing not provided over the entire surface.

6. The multi-layer oral thin film according to claim 1, wherein the at least two layers are connected to one another by two sealings not provided over the entire surface.

7. A method for producing a multi-layer oral thin film comprising the steps of
   a) providing a first layer comprising at least one water-soluble polymer;
   b) providing a further layer comprising at least one water-soluble polymer and having the same size and area as the first layer; wherein at least one of the layers provided in step a) and/or step b) contains at least one pharmaceutical active ingredient;
   c) arranging the first layer on the further layer; and d) performing at least one sealing, which covers no more than 66% of a total surface of the multi-layer oral thin film, in order to connect the first layer and the further layer to one another, provided that the at least one sealing is applied in such a way that at least one overlapping edge of the at least two layers arranged one on top of the other is not closed by a sealing as to allow saliva to infiltrate between the individual layers.

8. The method for producing a multi-layer oral thin film according to claim 7, wherein the at least one sealing performed in step d), not provided over the entire surface, is a heat-sealing not provided over the entire surface.

9. A multi-layer oral thin film obtained by the method of claim 7.

10. A method of administering a medicament comprised of the multi-layer oral thin film of claim 1, the method comprising oral administration.

11. The multi-layer oral thin film according to claim 1, wherein the at least one sealing is not adhesive.

12. The multi-layer oral thin film according to claim 1, wherein each of the at least two layers of the multi-layer oral thin film include at least one pharmaceutical active ingredient.

13. The multi-layer oral thin film according to claim 1, wherein the at least two layers are arranged congruently one on top of the other.

14. The method for producing a multi-layer oral thin film according to claim 8, wherein the heat-sealing is performed between 50° C. and 200° C. for 5 seconds or less.

* * * * *